United States Patent [19]

Hobbs et al.

[11] 4,100,194
[45] Jul. 11, 1978

[54] PRODUCTION OF UNSATURATED AMINES EMPLOYING A PALLADIUM COMPOUND CO-CATALYZED WITH A PHOSPHONITE LIGAND

[75] Inventors: Charles F. Hobbs, Des Peres; Dudley E. McMackins, St. Charles, both of Mo.

[73] Assignee: Monsanto Company, St. Louis, Mo.

[21] Appl. No.: 747,835

[22] Filed: Dec. 6, 1976

Related U.S. Application Data

[62] Division of Ser. No. 697,900, Jun. 21, 1976.

[51] Int. Cl.$^2$ .................... C07C 85/18; C07C 87/45; C07C 87/54; C07C 87/62
[52] U.S. Cl. .................... 260/576; 252/431 C; 252/431 N; 252/431 P; 260/293.51; 260/326.8; 260/563 R; 260/563 C; 260/577; 260/583 H; 26/583 P; 260/585 D; 544/178; 544/404

[58] Field of Search .................... 260/577, 576, 585 D; 252/431 C, 431 N, 431 P

[56] References Cited

U.S. PATENT DOCUMENTS 3,502,725   3/1970   Dewhirst et al. .................... 260/577

OTHER PUBLICATIONS

Baker et al., "J. Chem. Soc., Perkin Trans. 2," pp. 1511–1517 (1974).

*Primary Examiner*—Daniel E. Wyman
*Assistant Examiner*—John J. Doll
*Attorney, Agent, or Firm*—Scott J. Meyer; John D. Upham

[57] ABSTRACT

N-(alkadienyl)amines are produced at a rapid rate and in high yield by the reaction of conjugated dienes with ammonia and amines in a hydroxylic solvent using a catalyst system comprising a palladium compound co-catalyzed with a phosphonite ligand.

10 Claims, No Drawings

PRODUCTION OF UNSATURATED AMINES EMPLOYING A PALLADIUM COMPOUND CO-CATALYZED WITH A PHOSPHONITE LIGAND

This is a division of application Ser. No. 697,900, filed June 21, 1976.

BACKGROUND OF THE INVENTION

This invention relates to the palladium-catalyzed amination of conjugated dienes to produce long-chain unsaturated amines.

Recently, several publications have reported on the palladium-catalyzed linear dimerization of conjugated dienes, such as butadiene, with addition of amines; Takahashi, Bull. Chem. Soc. Japan 41, 454-60 (1968). According to one of these methods, the palladium catalyst is modified with a phenoxide anion catalyst promoter as described in U.S. Pat. Nos. 3,350,451 and 3,444,202. Another reported method employs a palladium complex with phosphine ligands such as triethylphosphine, tributylphosphine and triphenylphosphine; U.S. Pat. No. 3,530,187 and British Patent Specification No. 1,178,812. In all of these methods, long-chain amines are synthesized by use of primary or secondary amines in the amination reaction.

In still another publication, the direct amination of butadiene with ammonia is described by Mitsuyasu et al; Chem. Comm. (Japan), 345 (1971). The reaction is reported to take place in acetonitrile solvent and in the presence of palladium acetate and triphenylphosphine. However, the reaction is narrow in scope and sensitive to conditions. Moreover, the rates of amination using the catalyst system described by Mitsuyasu are low and yields are poor.

Development of a practical method for the rapid addition of ammonia or amines to butadiene to produce long-chain unsaturated amines in high yields would provide significant advantages in simplicity of reaction and cost reduction.

BRIEF DESCRIPTION OF THE INVENTION

It has now been discovered that long-chain unsaturated amines can be produced at a rapid rate and in high yield by the reaction of conjugated dienes with ammonia and amines in a hydroxylic solvent medium in the presence of a novel catalyst system comprising a palladium compound co-catalyzed with a phosphonite ligand. This reaction is more reactive than systems previously disclosed and proceeds under mild conditions of temperature.

According to another aspect of the invention, the addition of fluorinated solvents to the reaction medium enables the partitioning of the amine products in a liquid phase separate from the bulk of the catalyst solution. This solvent addition thereby facilitates the separation of the product and the recycle of the catalyst.

DETAILED DESCRIPTION OF THE INVENTION

Organic amines find a wide range of commercial usage such as rubber and paper chemicals, plasticizer intermediates, surfactants, water treatment chemicals and extractants. The long-chain unsaturated amines produced herein include N-(alkadienyl)amines such as, for example, bis(2,7-octadienyl)-amine and tris(2,7-octadienyl)amine, and minor amounts of branched chain amines, such as, for example, 1-vinyl-5-hexenyl amines. The unsaturated ethylenic linkages in these compounds can be hydrogenated to form the corresponding saturated amines or can be hydroxylated or hydrated to form useful alcohol derivatives from which esters or ethers are prepared. The ethylenic linkage serves as a dienophile in Diels-Alder condensations and also as a reactive site in polymerization processes. The amino moieties can be oxidized to form amine-N-oxides which are useful detergents or are reacted with alkyl halides to form tertiary or quaternary ammonium salts which are useful as surfactants and germicides.

In accordance with the present invention, an improved method for the preparation of the foregoing long-chain amines is provided. The invention resides in a new palladium-based catalyst system capable of direct amination of conjugated olefins with ammonia and amines to provide excellent yields of product and reaction rates under mild conditions. For example, the reaction with ammonia affords yields of amines as high as 98% in reaction times as short as one hour and at temperatures less than 70° C. These results represent a significant and substantial improvement over the amination process with ammonia reported by Mitsuyasu et al, supra, which requires ten hour reaction time at 80° C. In attempts to duplicate the Mitsuyau work, yields of only up to 37% were obtained at 80° C in ten hours.

The novel palladium-based catalyst system of this invention comprises a palladium compound and a phosphonite ligand which are employed in a hydroxylic solvent medium. The preferred palladium compounds are salts with readily displaceable anions such as, for example, acetate, nitrate and trifluoroacetate. The acetoacetate is substantially less effective and salts with strongly bound anions such as halides are ineffective in this catalyst system.

Other suitable palladium compounds are the sulfonic acid esters such as, for example, tetrakis-(benzonitrile)-palladium(II)trifluoromethanesulfonate and palladium-(II)tetrakis(acetonitrile)trifluoromethanesulfonate.

The foregoing palladium compounds which are preferably employed in the catalyst system advantageously are commercially available and do not need to be preformed in a separate step. The most preferred of these compounds is palladium acetate. It will be appreciated, however, that mixtures of these palladium compounds also can be used.

The preferred phosphonite ligands employed in this invention are dialkyl arylphosphonites having from about 3 to about 6 carbon atoms in the alkyl group such as, for example, diisopropyl phenylphosphonite, ditertiarylbutyl phenylphosphonite and dicyclohexyl phenylphosphonite. Other suitable phosphonite ligands are, for example, dialkyl phenylphosphonites having from one to about eight carbon atoms in the alkyl group such as dimethyl, diethyl, dipropyl, dibutyl, dipentyl, dihexyl, diheptyl and dioctyl phenylphosphonites, and also diphenyl phenyolphosphonite.

The phosphonites have an added advantage over certain phosphines of the prior art in their not being pyrophoric as are, for example, phosphines such as triethylphosphone. Certain other phosphines such as triphenylphosphine are ineffective under the conditions of the present catalyst system.

The amount of phosphonic ligand used can vary somewhat but best results are obtained with a ligand-/palladium compound mole ratio of from about 1.5/1 to about 4/1. The preferred ligand/palladium compound ratio is about 2.8/1.

Examples of conjugated dienes which can be appropriately aminated with ammonia by the aforesaid catalyst system of this invention are dienes having from four to about six carbon atoms such as, for example, butadiene, isoprene, 1,3-pentadiene, 2,4-hexadiene and 2,3-dimethylbutadiene. Certain larger molecules having a conjugated diene function such as 1,3,7-octatriene also can be aminated in accordance with this invention. Amination of butadiene is preferred.

Although a principal advantage of the invention resides in the direct amination with ammonia, it will be appreciated that amines also can be used with the novel catalyst system of this invention. Examples of suitable amines are monoalkylamines having from one to about 20 carbon atoms such as methylamine, ethylamine, propylamine, isopropylamine, butylamine, hexylamine, octylamine, octadecylamine, cyclohexylamine, cyclopentylamine, adamantylamine and ethanolamine; dialkylamines having from one to about 20 carbon atoms such as dimethylamine, diethylamine, dipropylamine, dibutylamine, dihexylamine, dioctylamine, dicyclohexylamine, N-methylcyclohexylamine and diethanolamine; alkenylamines such as allylamine, 2-butenylamine and 3-butenylamine; dialkenylamines such as diallylamine, dibutenylamine, 2,7-octadienylamine and bis-2,7-octadienylamine; heterocyclic amines such as pyrrolidine, piperidine, morpholine and piperazine; aromatic amines having from one to about 20 carbon atoms such as aniline, methylaniline, phenylenediamines and N-phenylphenylenediamines; and alkylenediamines having from one to about 20 carbon atoms such as ethylenediamine, trimethylenediamine, tetramethylenediamine, pentamethylenediamine, hexamethylenediamine and octamethylenediamine.

The proportions of conjugated diene and ammonia or amine used in the palladium-catalyzed reaction of this invention can vary widely. Thus, at butadiene/ammonia mole ratios of 0.5 or higher, the predominant product is tris(2,7-octadienyl)amine. At lower ratios of butadiene/ammonia, a shift to the bis(2,7-octadienyl)amine is obtained. With regard to rate of reaction, best results are obtained with a butadiene/ammonia ratio of from about 3/1 to about 6/1.

The proportions of ammonia or amine and the palladium compound also can vary widely and will depend in part upon the time and temperature of reaction. The preferred ratio of ammonia/palladium compound is from about 50/1 to about 250/1. In the case of the amines, the ratio of amine/palladium compound can range up to about 1000/1.

It has been found that use of a hydroxylic solvent for the reaction medium facilitates the rapid reaction rate. Solvents such as, for example, methanol, ethanol, propanol and phenol are preferred. Other suitable solvents are, for example, the glycols such as ethylene glycol, diethylene glycol and propylene glycol and various other hydroxylic solvents such as butanol and 2,2,2-trifluoroethanol. Nonhydroxylic solvents such as acetonitrile, tetrahydrofuran, chlorobenzene, nitrobenzene, ethyl acetate, and diethylether have been found ineffective in the catalyst system of this invention.

As mentioned above, another aspect of the invention resides in the addition of a fluorinated solvent to the reaction medium. Addition of these fluorinated solvents such as, for example, trifluoroacetic acid, 2,2,2-trifluoroethanol, and trifluoromethanesulfonic acid, results in a two-phase liquid product. For example, with use of trifluoroacetic acid the upper phase consists of predominantly amine products with a small portion of solvent while the lower phase consists of a solution of palladium compound, phosphonite ligand and ammonium trifluoroacetate in the remainder of the solvent. This partitioning provides a useful method for facile separation of product and re-use of the catalyst solution.

Although Kiji et al, Chem. Comm. (Japan), 770 (1973), reports that the addition of trifluoroacetic acid facilitates the nickel-catalyzed amination of butadiene with amines, trifluoroacetic acid is not a necessary component of the palladium-catalyzed amination herein. The useful solvent partitioning obtained with trifluoroacetic acid was unexpected in the present catalyst system.

Although reaction temperatures for the catalyst system defined herein can range from about 0° to about 150° C, temperatures of from about 50° to about 80° C are preferred in the case of using ammonia while temperatures of from about 25° C to about 60° C are preferred when using amines. At temperatures substantially higher than 150° C, the dimerization of the butadiene becomes increasingly competitive while at temperatures substantially lower than 0° C the reaction proceeds undesirably slowly.

The following detailed examples will further illustrate the invention although the invention is not limited to these specific examples.

Examples 1 to 12 illustrate the reaction of ammonia with butadiene whereas Examples 13 to 29 illustrate the reaction of primary and secondary amines with butadiene. Example 30 illustrates the reaction of ammonia with isoprene.

EXAMPLE 1

A reaction illustrating the invention was run in a 45-ml, stainless steel bomb equipped with a glass-covered magnetic stirrer. Solid and liquid reactants were charged into the bomb under a nitrogen atmosphere. Gaseous reactants were added by condensing them into the Dry Ice cooled bomb. In this reaction, 0.25 gram (1.1 millimole) of palladium acetate, 0.7 gram (3.1 millimoles) of diisopropylphenylphosphonite, 0.85 gram (0.05 mole) of ammonia, 12.9 grams (0.24 mole) of 1,3-butadiene, and 5 milliliters of ethanol were heated with stirring for one hour at 60° C. Autogenous pressure was less than 250 psig. The products, consisting of a mixture of bis(octadienyl)amines and tris(octadienyl) amines, were identified by VPC and mass spectroscopy. The total conversion of butadiene to octadienylated amines was 98%.

EXAMPLE 2

The procedure of Example 1 was repeated using the same reactants and conditions except that 1.36 grams (0.08 mole) of ammonia were charged and 2.5 grams (0.022 mole) of trifluoroacetic acid were added to the reactants. The octadienyl amine products separated into a phase apart from the catalyst solution and were removed by decantation. The catalyst solution was then reused for further amination with substantially equivalent excellent results. VPC analysis of the amine products in this Example was virtually identical to the VPC analysis from the single-phase reaction in Example 1.

Isolation of products for purposes of identification was accomplished by stripping solvent from the product layer and distillation of the residual liquid. Structural assignments were also made on the basis of VPC/mass spectroscopy. Tris(2,7-octadienyl)amine was isolated in greater than 99% purity, b.p. 164°–166° C (0.1 mm). Elem. anal.: Calc'd. for $C_{29}H_{39}N$: C, 84.37; H, 11.53; N, 4.10. Found: C, 84.45; H, 11.38; N, 4.27.

The unsaturated amine product mixtures were also hydrogenated using a nickel-on-kieselguhr catalyst (Harshaw Ni-0104) to give the corresponding dioctylamines and trioctylamines. These were then identified by gas chromatography and mass spectroscopy.

Analysis of the product mixture from the butadiene-ammonia reaction by VPC and mass spectroscopy showed the presence of two isomers of bis(octadienyl)amine and two isomers of tris(octadienyl)amine in 98% yield (based on butadiene). A small amount of the butadiene dimer, 4-vinylcyclohexane, was also seen. Four or five additional components were detected but in traces too small to readily identify.

The structure and the locations of the double bonds in tris(2,7-octadienyl)amine were confirmed by 270 MHz proton nuclear magnetic resonance.

EXAMPLE 3

Butadiene (0.24 mole), ammonia (0.08 mole), palladium acetate (1.11 millimole), diisopropylphosphonite (1.7 millimole), and 5 ml of methanol were reacted for one hour at 80° C in a manner similar to that of Example 1. The conversion to octadienyl amines was 95% (based on butadiene). When the non-hydroxylic solvent acetonitrile was used instead of the methanol solvent, the conversion to amines was 0%.

EXAMPLE 4

Example 3 was repeated except that phenol was substituted for the methanol solvent. The conversion to octadienyl amines was 67% (based on butadiene).

EXAMPLE 5

Example 3 was repeated except that ethanol was substituted for the methanol solvent. The conversion to octadienyl amines was 56%. (based on butadiene).

EXAMPLE 6

Butadiene (0.24 mole), ammonia (0.08 mole), palladium acetate (1.11 millimole), diisopropylphenylphosphonite (3.1 millimoles) and 5 ml. of ethanol were reacted for one hour at 70° C in a manner similar to that of Example 1. The conversion to octadienyl amines was 72% (based on butadiene). When palladium acetoacetate was used instead of the palladium acetate, the yield of octadienylamines was only 5%.

EXAMPLE 7

Example 6 was repeated except that an equivalent amount of palladium nitrate was substituted for the palladium acetate. The conversion to octadienyl amines was 67% (based on butadiene).

EXAMPLE 8

Example 6 was repeated except that an equivalent amount of tetrakis(benzonitrile)palladium(II)trifluoromethane sulfonate was substituted for the palladium acetate and the reaction temperature was 60° C. The conversion to octadienyl amines was 71% (based on butadiene).

EXAMPLE 9

Example 6 was repeated except that an equivalent amount of palladium(II)tetrakis(acetonitrile)trifluoromethane sulfonate was substituted for the palladium acetate and the reaction temperature was 80° C. The conversion to octadienyl amines was 68% (based on butadiene).

EXAMPLE 10

Butadiene (0.24 mole), ammonia (0.08 mole), palladium acetate (1.1 millimole), dicyclohexylphenylphosphonite (3.1 millimole) and 5 ml. of ethanol were reacted for one hour at 70° C in a manner similar to that of Example 1. The conversion to octadienyl amines was 73%. (based on butadiene).

EXAMPLE 11

Butadiene (0.24 mole), ammonia (0.08 mole), palladium acetate (1.11 millimole), diisopropylphenylphosphonite (3.1 millimoles), trifluoromethanesulfonic acid (20 millimoles) and 5 ml. of ethanol were reacted for one hour at 60° C. The octadienylated amine products separated into a phase apart from the catalyst solution and were removed by decantation. Conversion to octadienyl amines was 65% (based on butadiene).

EXAMPLE 12

Butadiene (0.24 mole), ammonia (0.08 mole), palladium acetate (1.1 millimole), diisopropylphenylphosphonite (3.1 millimoles) and 5 ml. of 2,2,2-trifluoromethanol were heated with stirring for one hour at 60° C. The octadienyl amine products separated into a phase apart from the catalyst solution and were removed by decantation. The conversion to octadienyl amines was 83% (based on butadiene).

In the following examples, Examples 13 to 23 illustrate amination of butadiene with primary and secondary aliphatic amines while Examples 24 to 29 illustrate amination with aromatic amines using the palladium acetate/diisopropylphenylphosphonite ligand catalyst system of this invention. The process employing the aliphatic amines proceeds at 60° or less, often exothermically, and is complete in 30 minutes to 4 hours, depending on the basicity of the amine. The catalyst is recoverable in active form in most cases either by stripping off the product, when it is low boiling, or by forming a two-phase reaction mixture in the case of higher molecular weight products. The reactions were run in either a 300 ml. or a 600 ml. stainless steel stirred autoclave equipped with a pressure gauge.

In Examples 13 to 23, 0.83 gram (3.7 mole) of palladium acetate, 17 ml. of methanol, 2.3 grams (10.3 mole) of diisopropylphenylphosphonite, and 0.80 mole of primary or secondary amine were charged to the autoclave under nitrogen. A partial vacuum was applied to the autoclave, and it was then cooled in a Dry Ice bath while butadiene was condensed in. The charge of butadiene was 3.2 moles in the case of primary amines and 1.6 moles when secondary amines were used.

The reaction mixture was then allowed to warm to room temperature. In cases where an exotherm was noted, cooling was applied to control the reaction at about 60° C. When no exotherm was noted after stirring the mixture for 15 to 30 minutes at room temperature, the mixture was heated to 60° C. Pressures generated were generally in the 50 psi or less range, except for methylamine and dimethylamine where initial pressures up to 100 psi were generated. The reactions were allowed to proceed until the internal pressure dropped to near zero.

The homogeneous product was distilled at low pressure through a short-path head to separate it from the catalyst and then was fractionally distilled. Identification and structure assignments were made on the basis of VPC, proton nuclear magnetic resonance, and elemental analysis.

For the two-phase catalyst system, the above procedure was repeated with 1.8 grams (0.05 mole) of ammonium trifluoroacetate added to the original charge reactants. The amine products formed a phase separate from the catalyst solution and were decanted for fractional distillation.

Most of the reactions gave near quantitative conversions to octadienylated tertiary amines as shown by VPC. The products were predominantly those with straight chain $C_8$ groups with unsaturation in the 2 and 7 positions. Portions of each amine were also hydrogenated over nickel-on-kieselguhr to give the corresponding saturated amines.

The amines used in these examples and the results obtained were as follows:

| Ex. No. | Amine | Reaction Time (min.) | Reaction Temp. (° C.) | Conversion % amine, VPC |
|---|---|---|---|---|
| 13 | Morpholine | 30 | R.T.−80 | 100 |
| 14 | Dimethylamine | 60 | R.T.−60 | 100 |
| 15 | Diethylamine | 50 | R.T.−60 | 100 |
| 16 | Di-n-butylamine | 240 | R.T.−60 | 100 |
| 17 | Di-n-hexylamine * | 90 | R.T.−60 | 100 |
| 18 | Diethanolamine | 240 | R.T.−60 | 100 |
| 19 | Pyrrolidine | 30 | 60 | 100 |
| 20 | Methylamine | 180 | 60 | 100 |
| 21 | Ethylamine | 210 | 60 | 100 |
| 22 | n-Butylamine | 180 | 25-60 | 95-100 |
| 23 | Ethanolamine | 60 | 60 | 95-100 |

* Two-phase reaction using ammonium trifluoroacetate

In Example 24, the reaction with aniline proceeded under the same conditions used with the aliphatic amines of Examples 13-23 to give predominantly 2,7-octadienylated amines.

In Examples 25 to 29, the ammonium reaction was applied to p-phenylenediamine and N-phenyl-p-phenylenediamine, using ammonium trifluoroacetate to give two-phase reaction mixtures. The former amine readily underwent complete alkylation with four octadienyl groups to produce predominantly tetrakis (2,7-octadienyl)-p-phenylenediamine while the latter amine gave mixtures of various alkylated amines, depending upon the mole ratio of amine to butadiene.

| Ex. No. | Amine | Mole Ratio Butadiene/Amine | Reaction Time (min.) | Reaction Temp. (° C.) | Conversion % amine, VPC |
|---|---|---|---|---|---|
| 24 | aniline | 4 | 60 | 60 | 95-100 |
| 25 | p-phenylenediamine | 8 | 180 | 60 | 100 |
| 26 | " " | 4 | 335 | 50 | 95 |
| 27 | N-phenyl-p-phenylenediamine | 6 | 425 | 65 | 85 |
| 28 | " " | 4 | 115 | 60 | 90 |
| 29 | " " | 2 | 300 | 60 | 90 |

EXAMPLE 30

Isoprene (0.24 mole), ammonia (0.08 mole), palladium acetate (1.11 millimole), diisopropylphenylphosphonite (3.1 millimoles) and 5 ml. of ethanol were heated and stirred for one hour at 100° C to produce a mixture of $C_{15}$ to $C_{25}$ amines, with several isomers of each, in addition to the $C_{10}$ to $C_{15}$ oligomers of isoprene.

Various other examples will be apparent to the person skilled in the art after reading the present disclosure without departing from the spirit and scope of the invention and it is intended that all such examples be included within the scope of the appended claims.

What is claimed is:

1. The process of producing N-(alkadienyl)amines by reaction of a conjugated diene and an aromatic amine selected from the group consisting of aniline, methylaniline, phenylenediamines, and N-phenylphenylenediamines in a hydroxylic solvent medium in the presence of a catalyst comprising a palladium compound co-catalyzed with a phosphonite ligand.

2. The process of claim 1 in which the conjugated diene is butadiene.

3. The process of claim 1 in which the hydroxylic solvent is methanol.

4. The process of claim 1 in which the palladium compound is a salt of palladium and a readily replaceable anion.

5. The process of claim 1 in which the palladium compound is palladium acetate.

6. The process of claim 1 in which the phosphonite ligand is a dialkyl arylphosphonite having from about 3 to about 6 carbon atoms in the alkyl group.

7. The process of claim 1 in which the phosphonite ligand is diisopropyl phenylphosphonite.

8. The process of claim 1 in which the conjugated diene is butadiene, the hydroxylic solvent is methanol, the palladium compound is palladium acetate and the phosphonite ligand is diisopropyl phenylphosphonite.

9. The process of claim 1 in which a fluorinated solvent is employed as an additional component in the reaction medium to provide a two-phase liquid product whereby the amine product can be partitioned in a liquid phase separate from the bulk of the catalyst.

10. The process of claim 9 in which the fluorinated solvent is ammonium trifluoroacetate.

* * * * *